US006584357B1

(12) United States Patent
Dawson

(10) Patent No.: US 6,584,357 B1
(45) Date of Patent: Jun. 24, 2003

(54) METHOD AND SYSTEM FOR FORMING AN ACOUSTIC SIGNAL FROM NEURAL TIMING DIFFERENCE DATA

(75) Inventor: Thomas P. Dawson, Escondido, CA (US)

(73) Assignees: Sony Corporation, Tokyo (JP); Sony Electronics, Inc., Park Ridge, NJ (US)

( * ) Notice: Subject to any disclaimer, the term of this patent is extended or adjusted under 35 U.S.C. 154(b) by 153 days.

(21) Appl. No.: 09/690,786

(22) Filed: Oct. 17, 2000

(51) Int. Cl.$^7$ .................................................. A61N 1/00
(52) U.S. Cl. ......................................... 607/54; 128/897
(58) Field of Search ............................. 607/54; 128/897

(56) References Cited

U.S. PATENT DOCUMENTS

| | | | |
|---|---|---|---|
| 3,848,608 A | 11/1974 | Leonard | 128/419 R |
| 4,343,301 A | 8/1982 | Indech | 128/24 |
| 4,611,596 A | 9/1986 | Wasserman | 128/419 R |
| 4,628,933 A | 12/1986 | Michelson | 128/419 R |
| 4,664,117 A | * 5/1987 | Beck | 607/54 |
| 4,883,067 A | 11/1989 | Knispel | 128/732 |
| 4,979,508 A | 12/1990 | Beck | 128/419 R |
| 5,031,154 A | 7/1991 | Watanabe | 367/8 |
| 5,097,326 A | 3/1992 | Meijer | 358/94 |
| 5,109,844 A | 5/1992 | De Juan, Jr. et al. | 128/419 R |
| 5,159,927 A | 11/1992 | Schmid | 128/419 R |
| 5,179,455 A | 1/1993 | Garlick | 359/9 |
| 5,651,365 A | 7/1997 | Hanafy et al. | 128/622.03 |
| 5,738,625 A | * 4/1998 | Gluck | 600/9 |
| 5,853,370 A | 12/1998 | Chance | 600/473 |
| 5,935,155 A | 8/1999 | Humayun et al. | 607/54 |
| 5,956,292 A | 9/1999 | Bernstein | 367/140 |
| 5,971,925 A | 10/1999 | Hossack et al. | 600/443 |

OTHER PUBLICATIONS

Department of Electrical and Computer Engineering, University of Colorado, 1990, Richard T. Mihran, Frank S. Barnes, Howard Wachtel. "Transient Modification of Nerve Excitability in Vitro By Single Ultrasound Pulses".

Ultrasound Med Biol 1990, Department of Electrical and Computer Engineering, University of Colorado. "Temporally–specific modification of myelinated axon excitability in virto following a single ultrasound pulse" (pp. 297–309) Mihran RT; Barnes FS; and Wachtel H.

The Pennsylvaia State University, Department of Physics. 1984, J.D. Maynard, E.G. Williams, and Y. Lee. Nearfiled acoustic holography:n I. Theory of generalized holography and the development of NAH.

Department of Molecular and Cell Biology, Division of Neurobiology, University of California. Garrett B. Stanley, Fei F. Li, and Yang Dan. "Reconstruction of Natural Scenes from Ensemble Responses in the Lateral Geniculate Nucleus" The Journal of Neuroscience, pp 8036–8042; 1999.

ULTRASONICS Fundamentals, Technology, Applications. Dale Ensminger, Columbus, Ohio. (pp 373–376).

"Human hearing in connection with the action of ultrasound in the megahertz range on the aural labyrinth" 1979. L. R. Gavrilov, G. V. Gershuni, V.I. Pudov, A.S. Rozenblyum, and E.M. Tsirul'nikov. American Institute of Phusics pp. 290–292.

The Institute of Electrical and Electronics Engineers, Inc. 1996; Richard A. Normann, Edwin M. Maynard, K. Shane Guillory, and David J. Warren. "Cortical Implants for the Blind".

(List continued on next page.)

Primary Examiner—Carol Layno
(74) Attorney, Agent, or Firm—Mayer Fortkort & Williams, PC; Karin L. Williams, Esq

(57) ABSTRACT

A non-invasive system and process for converting sensory data, e.g., visual, audio, taste, smell or touch, to neural firing time differences in a human brain and using acoustic signals to generate the neural firing time differences. Data related to neural firing time differences, the acoustic signals, and a user's response map may be stored in memory. The user's response map may be used to more accurately map the calculated neural firing time differences to the correct neural locations.

32 Claims, 3 Drawing Sheets

OTHER PUBLICATIONS

Computational Neuroscience 13; Eric L. Schwartz, Bjorn Merker, Estarose Wolfson, and Alan Shaw. 1988. "Applications of Computer Graphics and Image Processing to 2D and 3D Modeling of the Functional Architecture of Visual Cortex".

CMPnet. The Technology Network. Feb. 10, 1997. "Treading fine line between man and machine, researchers pursue silicon prostheses—Chip implants: weird science with a noble purpose—Second of two parts" Larry Lange.

EETIMESonline, www.cmpnet.com; The Technology Network/ 1999; ;Craig Matsumoto, EE Times; ISSCC: "Papers outline biochips to restore eyesight, movement".

JN Online. The Journal of Neurophysiology, vol. 77 No. 6 1997, pp. 2879–2909, The Americal Physiological Society. "Encoding of Binocular Disparity by Complex Cells in the Cat's Visual Cortex".

Gttp:www.bionictech.com, Center for Neural Interfaces. Richard A. Normann, Ph.D.

BBC News Online Science, Dr. David Whithouse, Sci/Tech Computer uses cat's brain to see.

Kksbio@engr.psu.edu, PennState College of Engineering, The Whitaker Center for Medical Ultrasonic Transducer Engineering.

Dpmi.tu–graz.ac.at/research/BCI; Brain Computer Interface.

Ipaustralia.gov.au/fun/patents/02_ear.htm; Bionic Ear Patent; Melbourne University—Australian Patent 519851; filing date 1978.

Measurement and Projection of Acoustic Fields; Earl G. Williams; Nava Research Laboratory, Code 5137, Washing D.C. 20375.

Resonance, Newsletter of the Bioelectromagnetics Special Interest Group. pp. 11–13, 15–16. Judy Wall.

* cited by examiner

METHOD AND SYSTEM FOR FORMING AN ACOUSTIC SIGNAL FROM NEURAL TIMING DIFFERENCE DATA

CROSS REFERENCE TO RELATED APPLICATIONS

The present Application is related to the U.S. patent application Ser. No. 09/690,571 entitled "Method and System For Generating Sensory Data Onto The Human Neural Cortex," co-filed with the present patent application on even date, and assigned to the Assignee of the present invention, and is hereby incorporated by reference in its entirety.

BACKGROUND OF THE INVENTION

1. Field of the Invention

The present invention relates to a method and system for generating sensory experiences. In particular, the present invention relates to a method and system for forming an acoustic signal from neural timing difference data.

2. Description of Related Art

A conventional technique for generating neural activity in the human nervous system requires surgical implants. The implants may comprise electronic connections and wires that cause electronic impulses to interact with some portion of the human nervous system, such as the human neural cortex, and thereby cause neural activity in the human neural cortex. Researchers have successfully mapped audio sensory data to the cochlear channel, and visual data to the visual cortex.

Conventional invasive techniques have several drawbacks. First, surgical implants may cause patient trauma and medical complications during and/or after surgery. Second, additional or on-going surgery may be required, particularly if new technology is developed.

SUMMARY

The present invention solves the foregoing drawbacks by providing a non-invasive system and process that uses acoustic signals to generate sensory data, e.g., visual, audio, taste, smell or touch, within/onto the human neural cortex. The system forms acoustic signals from neural timing difference data.

One advantage of the system is its adaptability to each individual user. Human brains have some similarities, but they may vary in size, shape, number of convolutions, etc. The present system comprises components that may be calibrated and a library of acoustic signals that may be customized for each individual user. The system is advantageously configured to allow vision-impaired and/or hearing-impaired users to experience at least some visual and/or auditory sensations.

Another advantage of the system is that no invasive surgery is needed to assist a person, such as a blind or deaf person, to experience live or recorded images or sounds.

One embodiment of the system comprises a primary transducer array and a secondary transducer array. The primary transducer array acts as a coherent or nearly-coherent signal source. The secondary transducer array acts as a controllable, acoustic diffraction pattern that shapes, focuses and modulates energy from the primary transducer onto the neural cortex in a desired pattern. The secondary transducer emits acoustic energy that may be shifted in phase and amplitude relative to the primary array emissions.

The projected, ultrasonic sensory pattern of energy is configured such that each portion of the pattern projected into the neural cortex may be individually pulsed at low frequencies. The system produces low frequency pulsing by controlling the phase differences between the emitted energy of the primary and secondary transducer array elements. The ultrasonic signal pulsed at low frequencies affects the neural firing timing in the cortex. Even though a person may be blind or have his or her eyes closed, the person's visual cortex neurons are still firing. Changes in the neural firing timing induce various sensory experiences, depending on the altered firing time and the location of the neuron in the cortex. The mapping of some sensory areas of the cortex is known and used in current surgically invasive techniques. The present system induces recognizable sensory experiences by applying ultrasonic energy pulsed at low frequency in one or more selected patterns on one or more selected locations of the cortex.

One aspect of the invention relates to a method of storing data related to acoustic signals configured to alter neural firing times in a brain. The method comprises non-invasively projecting a first acoustic signal into the brain. The first acoustic signal affects a neural firing time at a first neural location in the brain. The method stores a user sensory response and data related to the first acoustic signal in a memory. The method non-invasively projects a second acoustic signal into the brain, and stores a user sensory response and data related to the second acoustic signal in the memory.

Another aspect of the invention relates to a method of customizing a library of data related to acoustic signals configured to alter neural firing times in a brain. The method comprises retrieving data related to a first acoustic signal from a memory; projecting a first acoustic signal into the brain using the data related to a first acoustic signal, the first acoustic signal affecting a neural firing time at a first neural location in the brain; storing a user sensory response with the data related to the first acoustic signal in the memory; retrieving data related to a second acoustic signal form the memory; projecting a second acoustic signal into the brain using the data related to the second acoustic signal; and storing a user sensory response with the data related to the second acoustic signal in the memory.

Another aspect of the invention relates to a system of storing data related to acoustic signals configured to alter neural firing times in a brain. The system comprises a transducer system configured to non-invasively project a first acoustic signal and a second acoustic signal into the brain, the first and second acoustic signal affecting one or more neural firing times at one or more neural locations in the brain; a signal generator coupled to the transducer system; and a memory coupled to the signal generator. The memory is configured to store: data related to the first and second acoustic signals; and user sensory responses produced by the first and second acoustic signals. The signal generator is configured to select data in the memory related to signals configured to generate the neural firing time differences in the brain, the transducer system is configured to apply the signals to generate the neural firing time differences in the brain.

The present invention will be more fully understood upon consideration of the detailed description below, taken together with the accompanying drawings.

BRIEF DESCRIPTION OF THE DRAWINGS

Use of the same reference symbols in different figures indicates similar or identical items.

DETAILED DESCRIPTION

Figure 1:
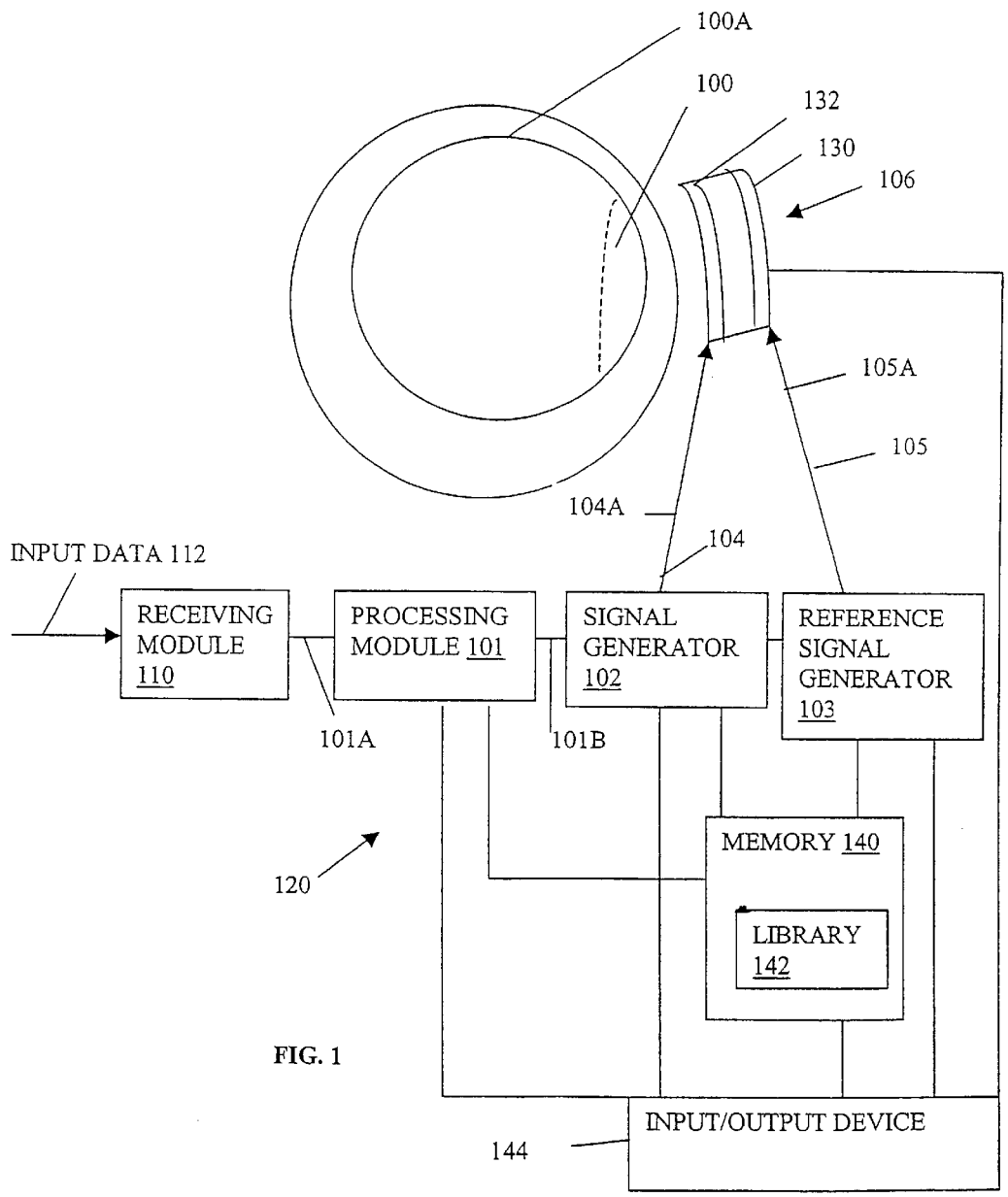
FIG. 1 illustrates one embodiment of a system for generating sensory data onto a human neural cortex.

FIG. 1 illustrates one embodiment of a system 120 for generating sensory data onto a human neural cortex. The system 120 comprises a receiving module 110, a processing module 101, a signal generator 102, a reference signal generator 103, a transducer system 106, a first signal line 104, a second signal line 105, a memory 140 and an input/output device 144. All of the components, except the memory 140 and the input/output device 144, are described in U.S. patent application Ser. No. 09/690,571 entitled "Method and System For Generating Sensory Data Onto The Human Neural Cortex," co-filed with the present patent application, which is assigned to the Assignee of the present invention, and is hereby incorporated by reference in its entirety.

One or more of the components illustrated in FIG. 1, such as the transducer system 106, may be specially configured to generate visual, audio, taste, smell and/or touch within the human neural cortex. In one embodiment, some or all of the components of FIG. 1 may be integrated in a light-weight, compact device that may be strapped to a user, e.g., in a backpack or belt pack.

In FIG. 1, the memory 140 is coupled to at least the signal generator 102 and/or the reference signal generator 103. The memory 140 may comprise any suitable type of memory that is preferably compact and adapted for fast memory access. The input/output device 144 is coupled to at least the memory 140. The input/output device 144 may comprise a keypad, a mouse, a display or other type of suitable input/output device that allows an administrator or user to calibrate the components of the system 120 and/or modify the data stored in the memory 140.

The memory 140 stores a library 142 of neural firing time data and/or neural firing time difference data. The system 120 uses the data in the library 142 to generate an acoustic signal or pattern which alters, e.g., speeds up or slows down, one or more neural firing times of the human brain 100A. The patterns may affect various portions of the brain 100A substantially simultaneously. For example, the transducer system 106 may use signal phase shifts between two ultrasonic sources, such as the primary and secondary transducer arrays 130, 132, to produce specific pulse patterns which modify the firing times of targeted neurons. In one embodiment, the transducer system 106 produces a high frequency pattern that is pulsed at low frequencies. Altering the neural firing times causes a user to perceive sensory experiences.

The resolution, color, accuracy and other characteristics of the generated sensory experiences may vary according to the type of transducers used, the amount of neural firing time data stored in the library 142, and the processing power and speed of the system 120. For example, high resolution may be achieved with a large amount of neural firing time data and transducer arrays configured to focus acoustic signals to very small areas of the brain 100A.

The neural firing time data is obtained by reversing or inverting the acts of a technique described in "Reconstruction of Natural Scenes from Ensemble Responses in the Lateral Geniculate Nucleus" by Garrett B. Stanley et al. in the Sep. 15, 1999 issue of the Journal of Neuroscience, which is hereby incorporated by reference in its entirety.

Garrett et al. describe a technique of reconstructing spatiotemporal natural scenes by linearly decoding ensemble responses within the lateral geniculate nucleus (177 cells) of a cat. The present method and system reverses Garret's technique in order to convert sensory data to neural firing time data and use a pattern of ultrasound signals based on the neural firing time data to alter neural firing times within the brain 100A. The altered neural firing times, i.e., neural firing time differences, generate sensory experiences for the user.

The use of single ultrasound pulses to modify nerve excitability is described in "Transient Modification of Nerve Excitability In Vitro by Single Ultrasound Pulses" by Mihran et al. found in the Department of Electrical and Computer Engineering, University of Colorado, 1990, paper #90-038, which is hereby incorporated by reference in its entirety. Human hearing and the action of ultrasound are described in "Human Hearing In Connection With The Action of Ultrasound In The Megahertz Range On The Aural Labyrinth" by L. R. Gavrilov in the Sov. Phys. Acoust. 26(4), July–August 1980 pages 290–292, which is hereby incorporated by reference in its entirety.

During manufacture of the system 120, a manufacturer may configure and store data in the memory 140, as well as calibrate the components of the system 120. The library 142 may comprise pre-determined or tested data related to different signals which are categorized into groups, such as signals generating visual experiences, signals generating auditory experiences, signals generating tactile experiences, etc. The groups may be further sub-categorized based on the size, shape, bright or dark, color, duration, pitch, etc. of the sensory experiences.

The library 142 may be complete, partially incomplete or substantially empty after manufacturing. An administrator at a user site may use the input/output device 144 to modify or add data in the library 142 based on responses from a current user or a previous user of the system 120.

In one embodiment, there is a library of various signals that may be applied to each neural location of the brain 100A or a part of the brain, such as the visual cortex 100. For example, if there are 100 neural locations mapped, then there may be 100 libraries of signals. As used herein, a neural location may comprise a single neuron or a group of neurons.

In one embodiment, there is a library of various signals for each transducer element in the primary and secondary transducer arrays 130, 132. The transducer arrays 130, 132 may be two-dimensional or three-dimensional arrays. A desired ultrasonic pattern in the brain 100A generated by the primary and secondary transducer arrays 130, 132 (e.g., phased arrays) may be calculated by adding the waves generated by each transducer element.

Figure 2:
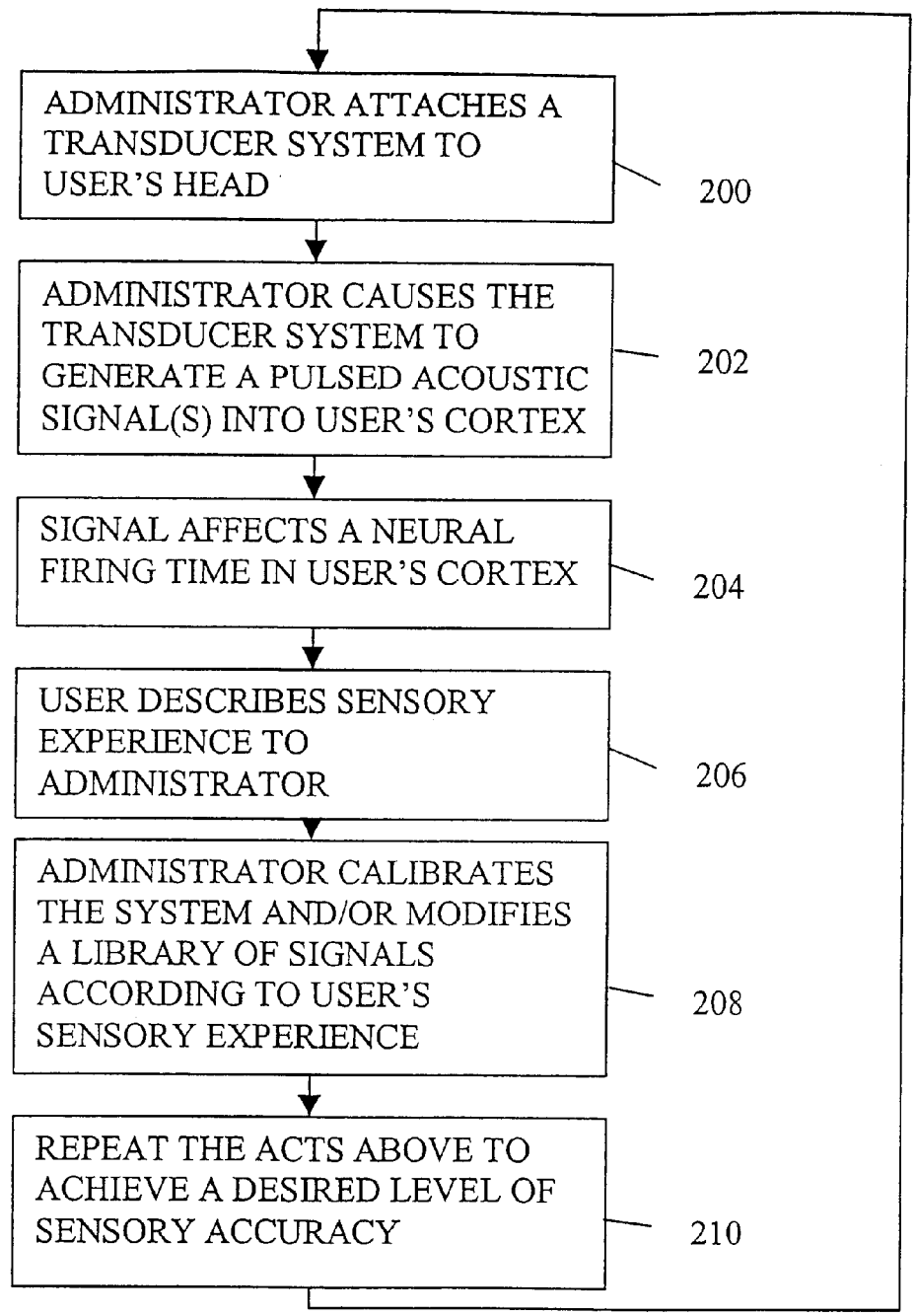
FIG. 2 illustrates a method for calibrating the system of FIG. 1 which generates sensory data onto a human neural cortex.

FIG. 2 illustrates a method for calibrating or configuring the system 120 of FIG. 1 which generates sensory data onto a human neural cortex of a particular user's brain 100A. In a start block 200, the administrator attaches the transducer system 106 in FIG. 1 non-invasively to a user's head and powers on the system 120. In one embodiment, the transducer system 106 is positioned near the back of the user's head to be closer to the visual cortex 100. The transducer system 106 may be attached and removed by the administrator or the user.

In a block 202, the administrator causes the transducer system 106 to generate a high frequency acoustic signal(s)/pattern pulsed at low frequencies into the user's brain 100A shown in FIG. 1. An initial signal may be called a 'test signal.'

In a block 204, the signal(s) affects, e.g., speeds up or slows down, one or more neural firing times in the user's brain 100A, such as the visual cortex 100.

In a block 206, the user describes a sensory experience to the administrator. For example, if the transducer system 106 is configured to generate sensory experiences in the visual cortex, the user may experience a flashing light, a ramp from a bright area to a dark area, or an object at a particular location of the user's simulated visual field. If the transducer system 106 is configured to generate sensory experiences in the cochlear channel, the user may experience a sound of a particular frequency, amplitude and duration.

In a block 208, the administrator may calibrate the system 120 based on the user's described sensory experience. For example, the administrator may calibrate the processing module 101, the signal generator 102, the reference signal generator 103 and/or the transducer system 106 based on the user's described sensory experience. If the signal was supposed to generate a bright white square in the top left corner of the user's simulated visual field, the administrator may calibrate the system 120 such that the user will perceive a bright white square the next time a signal is sent. The administrator may use the input/output device 144 or some other suitable device to calibrate the system 120.

Instead of or in addition to calibrating the system 120, the administrator may modify the data in the library 142 stored in the memory 140 based on the user's described sensory experience. The administrator may also enter new data associated with the primary and/or secondary transducer arrays 130, 132 into the library 142 with the input/output device 144.

In a block 210, the administrator may repeat the acts in blocks 200–208 a plurality of times to fill a partially incomplete library 142 and/or to achieve a level of sensory accuracy or resolution desired by the administrator or the user. Subsequent signals may vary in frequency, amplitude, duration and location. For example, the administrator may use the system 120 to create a map of various signals with various characteristics applied to various locations of the brain 100A or a part of the brain 100A that correspond to various perceived visual images.

In one embodiment, the administrator uses the system 120 to create a 'visual field' of perceived visual 'pixels' in memory 140 by testing a plurality of neural locations in the visual cortex 100. The 'pixel' may vary from light to dark or from colored to non-colored. The administrator may use the system 120 to map several degrees of light or color intensity for each pixel. The resolution of the visual field depends on (i) the focusing capability of the transducer system 106, (ii) a number of different neural locations tested by the administrator, and (iii) a number of different neural firing time differences applied at each neural location by the administrator slightly altering the amplitude, frequency, etc. of the test signal. Thus, the system components and/or the library 142 may be customized to each individual user.

Data in a library 142 may be transferred from memory 140 to other memories or to a database. Various transfer methods may be used, including wire, cable, and wireless communication systems.

Figure 3:
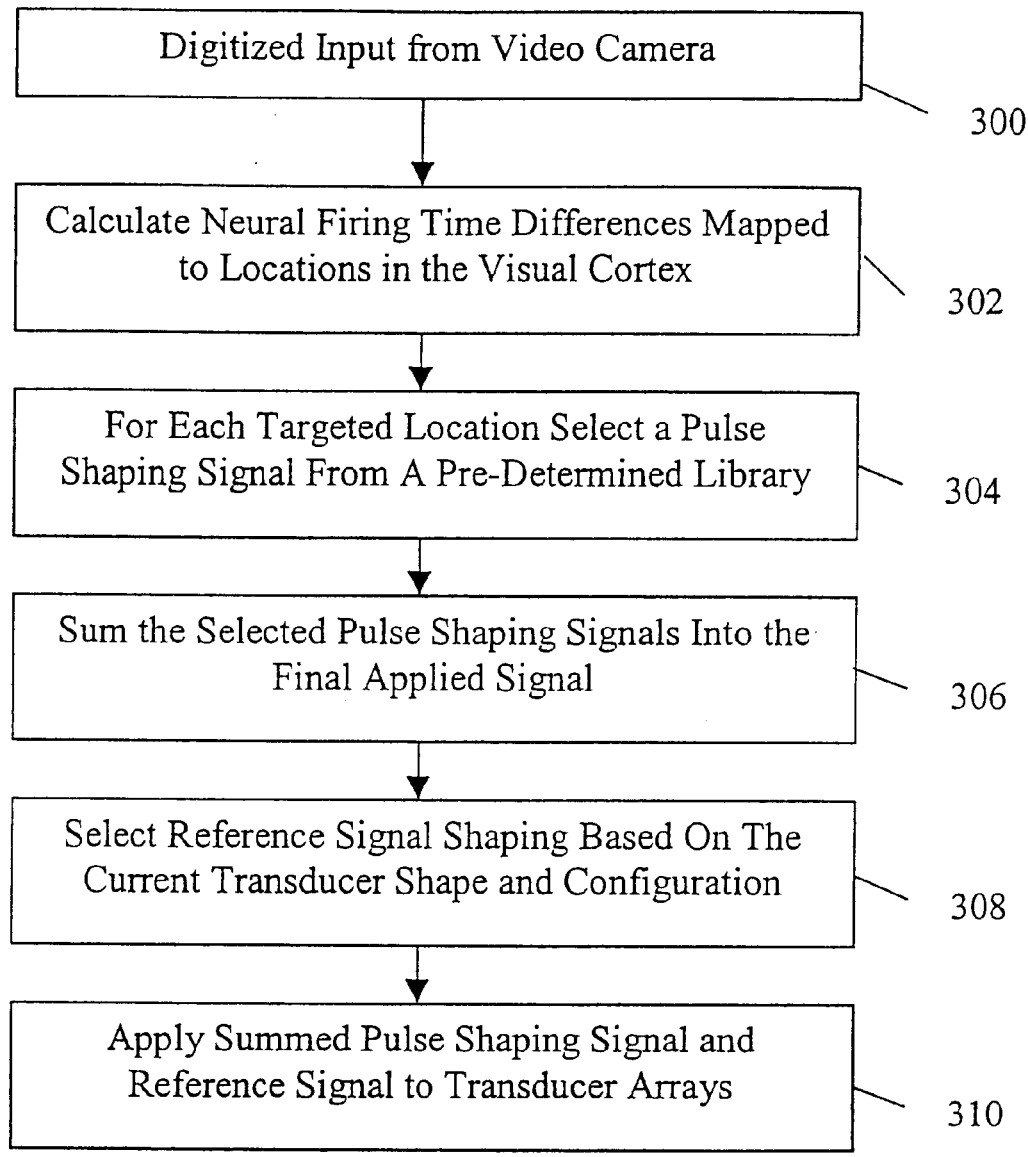
FIG. 3 illustrates a method of generating sensory data onto a human neural cortex with the system of FIG. 1.

FIG. 3 illustrates a method of generating sensory data onto a human neural cortex. The system 120 may be configured to generate live or recorded images, videos, textual pieces, sounds, audio pieces, smells, taste and tactile sensations. In a block 300, the receiving module 110 of FIG. 1 receives a sensory input from a video camera or other source, such as a VCR, a DVD player, a cable TV system, an Internet connection, etc. The sensory input may be transmitted by a wire or wireless communication system. For example, for a vision-impaired user, the video camera may be strapped on or near the user's head such that the angle of the camera changes as the user turns his or her head. Alternatively, the video camera may be configured to move according to a hand-controlled device, such as a computer game joy stick. The sensory input may comprise digital data or analog data. If the input data is analog, the processing module 101 may digitize the input data.

In a block 302, the processing module 101 and/or the signal generator 102 calculates neural firing time differences for mapped locations of the visual cortex 100 based on the sensory input.

In a block 304, the signal generator 102 selects data in the library 142 that will be used by the transducer system 106 to generate signals and achieve the desired neural firing time differences in the brain 100A. In one embodiment, the signal generator 102 selects data from the library 142 related to at least one pulse shaping signal, e.g., phase shift, for each targeted location in the visual cortex 100. For example, if there are 900 targeted locations in the visual cortex 100, then the signal generator 102 selects an individual pulse shaping signal from the library 142 for each of the 900 neural locations. The selected signals may vary in amplitude, phase, and/or duration.

In a block 306, the signal generator 102 sums the selected pulse shaping signals into a final applied signal or pattern for the secondary transducer array 132.

In a block 308, the reference signal generator 103 may select a reference signal shaping based on one or more factors, such as (1) the size, shape and configuration of the transducer system 106, and (2) the type of signals used by the secondary transducer array. The transducer system 106 may comprise a variety of transducer shapes, sizes, configurations, etc. Data related to various reference signals, including reference signals to generate a planar wave, may be stored in the library 142. The reference signals may be configured and stored by a manufacturer when the system 120 is manufactured and/or modified by an administrator at a user site.

The reference signals generated by the primary transducer array 130 may focus or shape the pattern generated by the secondary transducer array 132. The reference signals may vary in amplitude, phase, and/or duration from the signals selected by the signal generator 102.

In a block 310, the signal generator 102 applies a summed pulse-shaping signal to the secondary transducer array 132, and the reference signal generator 103 applies a reference signal to the primary transducer array 130. The transducer arrays 132, 130 generate a pulsed, ultrasound signal(s) or pattern comprised of phase shifts to the brain 100A, and the user experiences a sensory experience based on the sensory input from the video camera or other input source. The generated sensory experience may not be exact, but the generated sensory experience at least gives the user an idea of the sensory input. For example, depending on the implementation, a user using the system 120 may be able to only 'see' an outline of objects in front of the video camera.

In one embodiment, the ultrasound signals or pattern may be continuous, such that the user perceives a visual image in real-time as the video camera receives the image. In another embodiment, the ultrasound signals or pattern may be almost continuous, such that the user perceives a visual image in almost real-time, i.e., a string of snap shots, as the video camera receives the image.

Various types of memories, input/output devices, caches, controllers, registers and/or processing components may be used in accordance with the present invention. The scope of the present invention is not limited to a particular type of memory, input/output device, cache, controller, register and/or processing component. Various embodiments of the system 160 may comprise other components in addition to or instead of the components shown in FIG. 2 without departing from the scope of the invention. For example, the system 160 may comprise a sensory input device, additional memories, caches, controllers, registers and/or processing components.

The above-described embodiments of the present invention are merely meant to be illustrative and not limiting. It will thus be obvious to those skilled in the art that various changes and modifications may be made without departing from this invention in its broader aspects. The appended claims encompass all such changes and modifications as fall within the true spirit and scope of this invention.

What is claimed is:

1. A method of storing data related to acoustic signals configured to alter neural firing times in a brain, the method comprising:

non-invasively projecting a first acoustic signal into the brain, the first acoustic signal affecting a neural firing time at a first neural location in the brain;

storing a user sensory response and data related to the first acoustic signal in a memory;

non-invasively projecting a second acoustic signal into the brain; and storing a user sensory response and data related to the second acoustic signal in the memory.

2. The method of claim 1, wherein the first acoustic signal varies in amplitude from the second acoustic signal.

3. The method of claim 1, wherein the first acoustic signal varies in frequency from the second acoustic signal.

4. The method of claim 1, wherein the first acoustic signal varies in duration from the second acoustic signal.

5. The method of claim 1, wherein the second acoustic signal affects the neural firing time of the first neural location.

6. The method of claim 1, wherein the second acoustic signal affects the neural firing time of a second neural location.

7. The method of claim 6, further comprising:

non-invasively projecting additional acoustic signals into the brain, the additional acoustic signals affecting neural firing times at a plurality of neural locations in the brain; and storing user sensory responses and data related to the additional acoustic signals in a memory, wherein a map of neural locations, user sensory responses and data related to the acoustic signals is created.

8. The method of claim 7, further comprising categorizing the data related to the signals by targeted neural locations.

9. The method of claim 1, wherein non-invasively projecting at least one of the first and second acoustic signals comprises gating high frequency acoustic signals on then off at low frequencies.

10. The method of claim 1, wherein the first and second acoustic signals each comprise a pulsed signal generated by a primary transducer array and a secondary transducer array, the primary transducer array generating a reference wave and the secondary transducer array generating a diffraction pattern.

11. The method of claim 1, wherein the first and second acoustic signals are projected into a visual cortex of the brain.

12. The method of claim 11, wherein the first acoustic signal causes the user to perceive a first bright area in a simulated visual field, and the second acoustic signal causes the user to perceive a second bright area in the simulated visual field.

13. The method of claim 1, wherein the first and second acoustic signals are projected into a cochlear channel of the brain.

14. The method of claim 13, wherein the first acoustic signal causes the user to perceive a first sound in a simulated auditory range, and the second acoustic signal causes the user to perceive a second sound in the simulated auditory range.

15. A method of customizing a library of data related to acoustic signals configured to alter neural firing times in a brain, the method comprising:

retrieving data related to a first acoustic signal from a memory;

projecting a first acoustic signal into the brain using the data related to a first acoustic signal, the first acoustic signal affecting a neural firing time at a first neural location in the brain;

storing a user sensory response with the data related to the first acoustic signal in the memory;

retrieving data related to a second acoustic signal form the memory;

projecting a second acoustic signal in the brain using the data related to the second acoustic signal; and storing a user sensory response with the data related to the second acoustic signal in the memory.

16. The method of claim 15, wherein the second acoustic signal affects the neural firing time of the first neural location.

17. The method of claim 15, wherein the second acoustic signal affects the neural firing time of a second neural location.

18. The method of claim 15, wherein the first and second acoustic signals each comprise a pulsed signal generated by a primary transducer array and a secondary transducer array, the primary transducer array generating a reference wave and the secondary transducer array generating a diffraction pattern.

19. The method of claim 15, further comprising calibrating components that generate the first and second acoustic signals.

20. The method of claim 15, further comprising transferring the user sensory responses and the data in the memory to a second memory.

21. A method for projecting sensory data in a human brain, the method comprising:

receiving a sensory input;

calculating neural firing time differences for mapped neural locations in the brain based on the sensory input;

selecting data in a memory related to signals configured to generate the neural firing time differences in the brain; and projecting the signals to generate the neural firing time differences into the brain.

22. The method of claim 21, wherein the neural firing time differences cause the brain to experience the sensory input.

23. The method of claim 21, wherein the neural firing time differences cause the brain to experience a sensation that is similar to the sensory input.

24. The method of claim 21, wherein projecting the signals comprises:

emitting a first acoustic energy as a coherent signal source toward the brain; and producing a diffraction pattern for the first emitted acoustic energy, the diffraction pattern causing the neural firing time differences.

25. The method of claim 21, further comprising summing the signals configured to generate the neural firing time differences in the brain.

26. The method of claim 21, further comprising:

selecting a reference signal based on a type of transducer used to produce the signals configured to generate the neural firing time differences in the brain; and applying the reference signal to the brain, wherein signals configured to generate the neural firing time differences in the brain shape the pulse of the reference signal.

27. The method of claim 21, wherein the sensory input is selected from a group consisting of an image, a sound, a video, a textual piece, an audio piece, a smell, a taste and a tactile sensation.

28. A system of storing data related to acoustic signals configured to alter neural firing times in a brain, the system comprising:

a transducer system configured to non-invasively project a first acoustic signal and a second acoustic signal into the brain, the first and second acoustic signals affecting one or more neural firing times at one or more neural locations in the brain;

a signal generator coupled to the transducer system; and a memory coupled to the signal generator, the memory configured to store:

data related to the first and second acoustic signals; and user sensory responses produced by the first and second acoustic signals, wherein the signal generator is configured to select data in the memory related to signals configured to generate the neural firing time differences in the brain, the transducer system is configured to apply the signals to generate the neural firing time differences in the brain.

29. The system of claim 28, further comprising an input device configured to allow a user to modify the data into the memory.

30. The system of claim 28, further comprising an input device configured to allow a user to enter new data into the memory.

31. The system of claim 28, wherein the data related to the first and second acoustic signals are categorized by targeted neural locations.

32. The system of claim 28, further comprising:

a processing module coupled to the signal generator and the memory, the processing module being configured to calculate neural firing time differences for mapped neural locations in the brain based on a sensory input.

* * * * *